US007980132B2

(12) United States Patent
Gustin (10) Patent No.: US 7,980,132 B2
(45) Date of Patent: Jul. 19, 2011

(54) SENSOR ASSEMBLY HAVING A THERMALLY INSULATING ENCLOSURE

(75) Inventor: Ronald Ray Gustin, Washington, IL (US)

(73) Assignee: Caterpillar Inc., Peoria, IL (US)

( * ) Notice: Subject to any disclaimer, the term of this patent is extended or adjusted under 35 U.S.C. 154(b) by 505 days.

(21) Appl. No.: 12/230,231

(22) Filed: Aug. 26, 2008

(65) Prior Publication Data

US 2010/0050738 A1    Mar. 4, 2010

(51) Int. Cl.
G01D 11/24 (2006.01)
G01N 27/00 (2006.01)
(52) U.S. Cl. ........ 73/431; 73/23.31; 73/23.32; 73/866.5
(58) Field of Classification Search .............. 73/23.31, 73/23.32, 23.33, 23.34, 31.01, 31.02, 31.03, 73/431, 866.5
See application file for complete search history.

(56) References Cited

U.S. PATENT DOCUMENTS

| 4,339,318 | A |   | 7/1982  | Tanaka et al. |
|-----------|---|---|---------|---------------|
| 4,802,369 | A |   | 2/1989  | Morii |
| 4,980,042 | A | * | 12/1990 | Shiomi et al. ............... 204/427 |
| 5,505,073 | A |   | 4/1996  | Gerblinger et al. |
| 5,616,825 | A |   | 4/1997  | Achey et al. |
| 5,707,504 | A | * | 1/1998  | Jyouno et al. ............... 204/428 |
| 5,880,353 | A | * | 3/1999  | Graser et al. .................. 73/23.2 |
| 6,266,997 | B1 |  | 7/2001  | Nelson |
| 6,327,891 | B1 |  | 12/2001 | Noda et al. |
| 6,347,543 | B1 |  | 2/2002  | Geier et al. |
| 6,637,256 | B2 |  | 10/2003 | Shirai |
| 7,217,355 | B2 |  | 5/2007  | Nair et al. |
| 7,739,924 | B2 | * | 6/2010  | Lourdhusamy et al. ........ 73/863 |
| 7,841,769 | B2 | * | 11/2010 | Ma et al. ....................... 374/147 |
| 2002/0040599 | A1 | * | 4/2002 | Holleboom ..................... 73/431 |
| 2002/0069698 | A1 | * | 6/2002 | Wagner et al. ............... 73/118.1 |
| 2002/0100312 | A1 | * | 8/2002 | Jackson et al. ............... 73/31.05 |
| 2004/0011645 | A1 | * | 1/2004 | Beckmeyer et al. .......... 204/424 |
| 2006/0042946 | A1 | * | 3/2006 | Tsukahara et al. ............ 204/424 |
| 2006/0162422 | A1 |   | 7/2006 | Geier et al. |
| 2007/0089482 | A1 | * | 4/2007 | Uchikawa et al. ........... 73/23.32 |
| 2007/0277605 | A1 | * | 12/2007 | Fouts et al. ..................... 73/431 |
| 2008/0000667 | A1 | * | 1/2008 | Ruterbusch et al. ......... 174/16.1 |
| 2008/0017510 | A1 |   | 1/2008 | Nair et al. |

(Continued)

FOREIGN PATENT DOCUMENTS

EP          1445608 A1 *  8/2004

*Primary Examiner* — David A. Rogers
(74) *Attorney, Agent, or Firm* — Finnegan, Henderson, Farabow, Garrett & Dunner LLP (57) ABSTRACT

A sensor assembly is discussed. The sensor assembly may include a housing. The housing may include an inlet port and an outlet port. The sensor assembly may also include a sensing element disposed within the housing and extending along a longitudinal axis from a first end towards a second end. The sensing element may include heating elements. The sensor assembly may also include a sleeve circumferentially disposed about the sensing element. The sleeve may include a first passageway on a first side of the sensing element and a second passageway on an opposite second side of the sensing element. The first passageway and the second passageway may be longitudinal passageways extending along a length of the sensing element. The sleeve may also include an inlet orifice on one side of the sleeve and an outlet orifice on an opposite side of the sleeve. The inlet orifice may fluidly couple the inlet port with the first passageway and the outlet orifice may fluidly couple the outlet port with the second passageway.

20 Claims, 8 Drawing Sheets

U.S. PATENT DOCUMENTS

| | | |
|---|---|---|
| 2008/0067067 A1* | 3/2008 | Oya et al. .................... 204/426 |
| 2008/0282769 A1* | 11/2008 | Nelson ........................ 73/23.31 |
| 2009/0056416 A1* | 3/2009 | Nair et al. ................... 73/28.01 |
| 2009/0141769 A1 | 6/2009 | Baldwin |
| 2009/0211333 A1* | 8/2009 | Lourdhusamy et al. ..... 73/23.31 |
| 2009/0260987 A1* | 10/2009 | Valdes et al. ................. 204/424 |
| 2009/0319085 A1* | 12/2009 | Sell et al. ..................... 700/275 |
| 2010/0158758 A1* | 6/2010 | Gustin .......................... 422/83 |

* cited by examiner

SENSOR ASSEMBLY HAVING A THERMALLY INSULATING ENCLOSURE

TECHNICAL FIELD

The present disclosure relates generally to a sensor assembly, and more particularly, to a sensor assembly having a thermally insulating enclosure.

BACKGROUND

The composition of exhaust produced by the combustion of hydrocarbon fuels is a complex mixture of oxide gases ($NO_X$, $SO_X$, $CO_2$, CO, $H_2O$), unburned hydrocarbons, and oxygen. Measurement of the concentration of these individual exhaust gas constituents in real time can assist in improved combustion efficiency and lower emissions of polluting gases. Various devices have been proposed to operate as exhaust gas sensors that have the capability of measuring the concentration of a gas constituent in an exhaust stream. Some of these devices includes a ceramic sensing element encased in a housing and positioned in an exhaust stream. A part of the exhaust stream is directed into the housing to measure the concentration of some of the constituents of the exhaust. The ceramic sensing element may include sensing regions and heating elements configured to heat the sensing regions to a desired temperature range. The sensing region may measure the concentration of particular exhaust constituent with acceptable accuracy when the temperature of the sensing region is within the desired temperature range. A catalyst may also be used to condition the exhaust gases to increase the sensitivity of the sensor. During operation, a part of the exhaust from an engine may be directed over the sensing regions through the catalyst. The heating elements in the sensing element may heat the sensing regions and the catalyst to a high temperature to increase the accuracy and sensitivity of the measurements.

U.S. Pat. No. 7,217,355 (the '355 patent) issued to Nair et al. on May 15, 2007 discloses one such sensor. The sensor of the '355 patent includes a $NO_x$ sensor, catalyst, and a heating rod enclosed in a housing. The sensor of the '355 patent is configured to measure the concentration of $NO_x$ in an exhaust stream. The catalyst conditions the exhaust gases before being directed over the $NO_x$ sensor. The heating rod heats the $NO_x$ sensor and the catalyst, to increase the sensitivity of the sensor. This heat may also be conducted to the housing. In an application where it is desired to position such a sensor in an exhaust stream, the relatively cooler exhaust stream flowing over the housing may remove heat from the housing and thereby cool the sensor. This cooling of the sensor by the exhaust stream may compromise the accuracy of the sensor measurements. The disclosed sensor assembly is directed at overcoming shortcomings as discussed above and/or other shortcomings in existing technology.

SUMMARY

In one aspect, a sensor assembly is disclosed. The sensor assembly may include a housing. The housing may include an inlet port and an outlet port. The sensor assembly may also include a sensing element disposed within the housing and extending along a longitudinal axis from a first end towards a second end. The sensing element may include heating elements. The sensor assembly may also include a sleeve circumferentially disposed about sensing element. The sleeve may include a first passageway on a first side of the sensing element and a second passageway on an opposite second side of the sensing element. The first passageway and the second passageway may be longitudinal passageways extending along a length of the sensing element. The sleeve may also include an inlet orifice on one side of the sleeve and an outlet orifice on an opposite side of the sleeve. The inlet orifice may fluidly couple the inlet port with the first passageway and the outlet orifice may fluidly couple the outlet port with the second passageway.

In another aspect, a method of measuring a concentration of a constituent of exhaust gases using a sensor is disclosed. The method may include directing exhaust gases into a housing of the sensor through an inlet port. The method may also include conditioning the exhaust gases by passing the exhaust gases through a catalyst assembly. The catalyst assembly may be positioned in a first passageway of a sleeve. The sleeve may be positioned inside the housing and may be circumferentially disposed about a sensing element of the sensor. The first passageway may extend longitudinally along a first side of the sensing element. The method may also include passing the conditioned exhaust gases to a sampling chamber of the sensor. The sampling chamber may be a region of the sensor which included at least one sensing region of the sensor. The method may also include directing the exhaust gases from the sampling chamber to a second passageway of the sleeve. The second passageway may be disposed on a second side of the sensing element opposite the first side. The method may further include directing exhaust gas from the second passageway to outside the housing through an outlet port positioned opposite the inlet port.

In yet another aspect, a sensor assembly for measuring constituents of an exhaust gas is disclosed. The sensor assembly may include an external housing that may extend from a first end to a second end along a longitudinal axis, and a sensing element that may extend from the first end towards the second end. The sensor assembly may also include a substantially cylindrical sleeve located proximate the first end. The sleeve may be circumferentially disposed about the sensing element and may be positioned radially inwards of the housing. The sleeve may include a first passageway that may extend from a sampling chamber of the sensor assembly to an inlet orifice proximate the first end, along a first side of the sensing element. The sleeve may also include a second passageway that may extend from the sampling chamber to an outlet orifice proximate the first end, along a second side of the sensing element opposite the first side. The sensor assembly may further include a catalyst assembly disposed in the first passageway.

DETAILED DESCRIPTION

Figure 1:
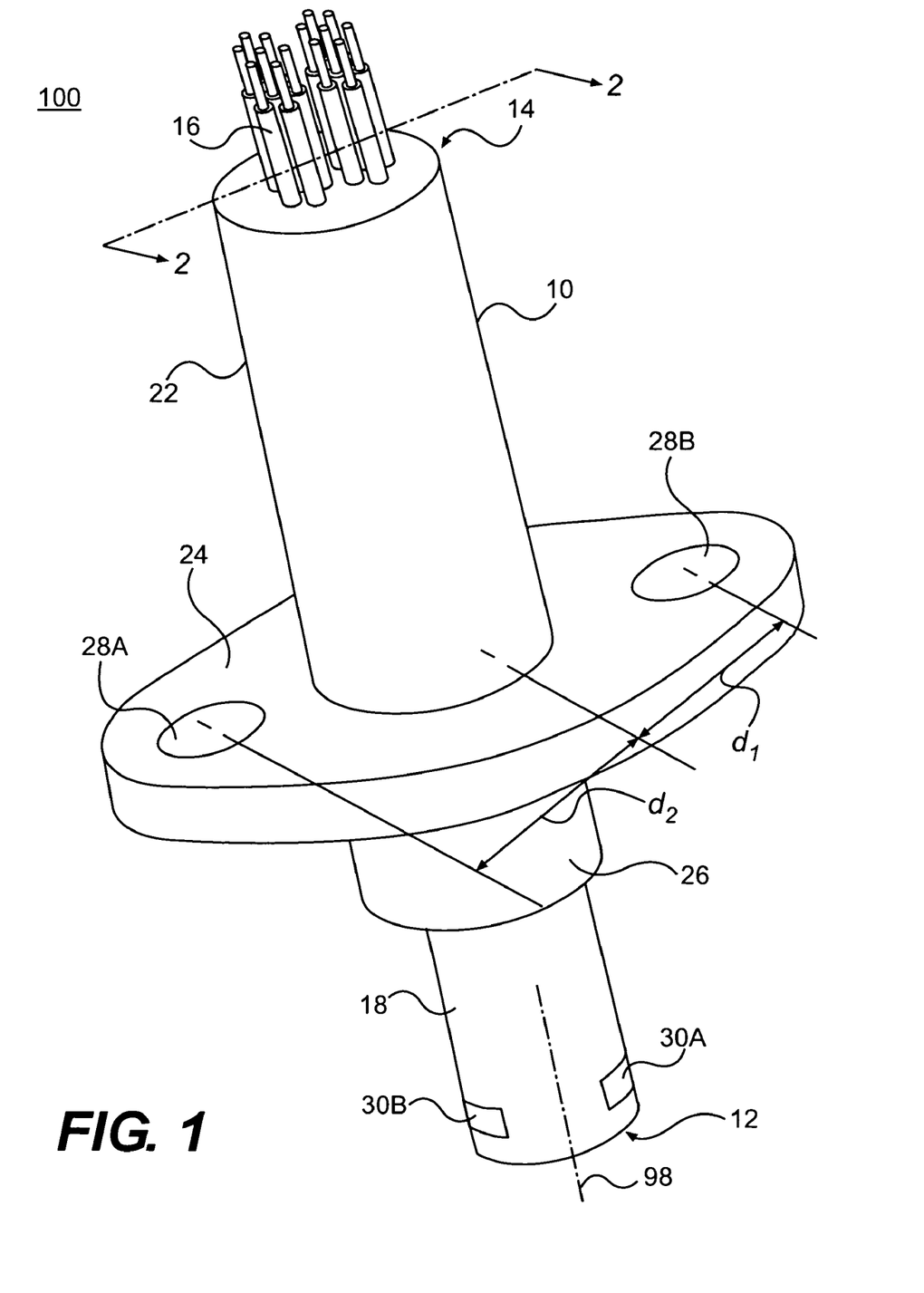
FIG. 1 is an illustration of an exemplary disclosed sensor assembly.

Referring to FIG. 1, the basic features of an exemplary disclosed sensor assembly 100 are illustrated. Sensor assembly 100 may be used to measure the constituents of a fluid in any application. In the description that follows, an embodiment of sensor assembly 100 configured to measure constituents of exhaust gases of an engine are described. In such an application, sensor assembly 100 may be coupled to a mounting fixture, and may be positioned in an exhaust duct that transports exhaust gases from the engine.

Sensor assembly 100 may include multiple components that cooperate to allow one or more constituents of the exhaust gas to be measured. The sensor assembly 100 may include a housing 10 having a first end 12 and a second end 14. The second end 14 may include one or more wire leads 16 extending therefrom. Housing 10 may have include an elongate body extending along a longitudinal axis 98. Housing 10 may also include a generally cylindrical first region 18 at first end 12, and a generally cylindrical second region 22 at second end 14. Second region 22 may have a different diameter than the diameter of the first region 18. Sensor assembly 100 may also include a mounting mechanism to mount the sensor assembly 100 to mounting features (not shown) on the exhaust duct of the engine. Any suitable mounting mechanism may be used for this purpose. In some embodiments, this mounting mechanism may include a flange 24 positioned between first region 18 and second region 22 of housing. Flange 24 may include a body 26 that extends normal to longitudinal axis 98, on two opposite sides of housing 10. Flange 24 may include cavities that may be used to couple sensor assembly 100 to the mounting features. These cavities may include a first cavity 28A and a second cavity 28B positioned on either side of housing 10. Although these cavities may have any general shape, in some embodiments, one or both of first cavity 28A and second cavity 28B may be circular. In some embodiments, the first cavity 28A and second cavity 28B may have different diameters, or may each be positioned at a different distance from longitudinal axis 98 (that is $d_1 \neq d_2$), to facilitate coupling of sensor assembly 100 to the mounting feature in a desired orientation. It is contemplated that, in place of these cavities, other keying features may be used to couple sensor assembly 100 to a mounting feature in a desired orientation.

First region 18 may include openings that may direct exhaust gases into, and out of, housing 10. In the embodiment depicted in FIG. 1, these openings include one rectangular inlet port 30A and one rectangular outlet port 30B on opposite sides of the cylindrical first region 18. However, it is contemplated that, other embodiments of sensor assembly 100 may include a different number and shape of openings. The orientation of these openings (inlet port 30A and outlet port 30B) with respect to the cavities (first cavity 28A and second cavity 28B) on flange 24 may be such that when sensor assembly 100 is positioned in the exhaust duct of the engine, the inlet port 30A may face the upstream side of the exhaust duct and outlet port 30B may face the downstream side. In such an orientation, the pressure of the exhaust gases flowing through the exhaust duct may drive a portion of these exhaust gases into housing 10. The obstruction in fluid flow, caused due to the presence of the sensor assembly 100, may create a zone of low pressure down stream of sensor assembly 100 (proximate outlet port 30B) due to known fluid mechanics mechanisms, such as, for example, the venturi effect. This low pressure zone may assist in drawing the exhaust gases out of housing 10.

Figure 2:
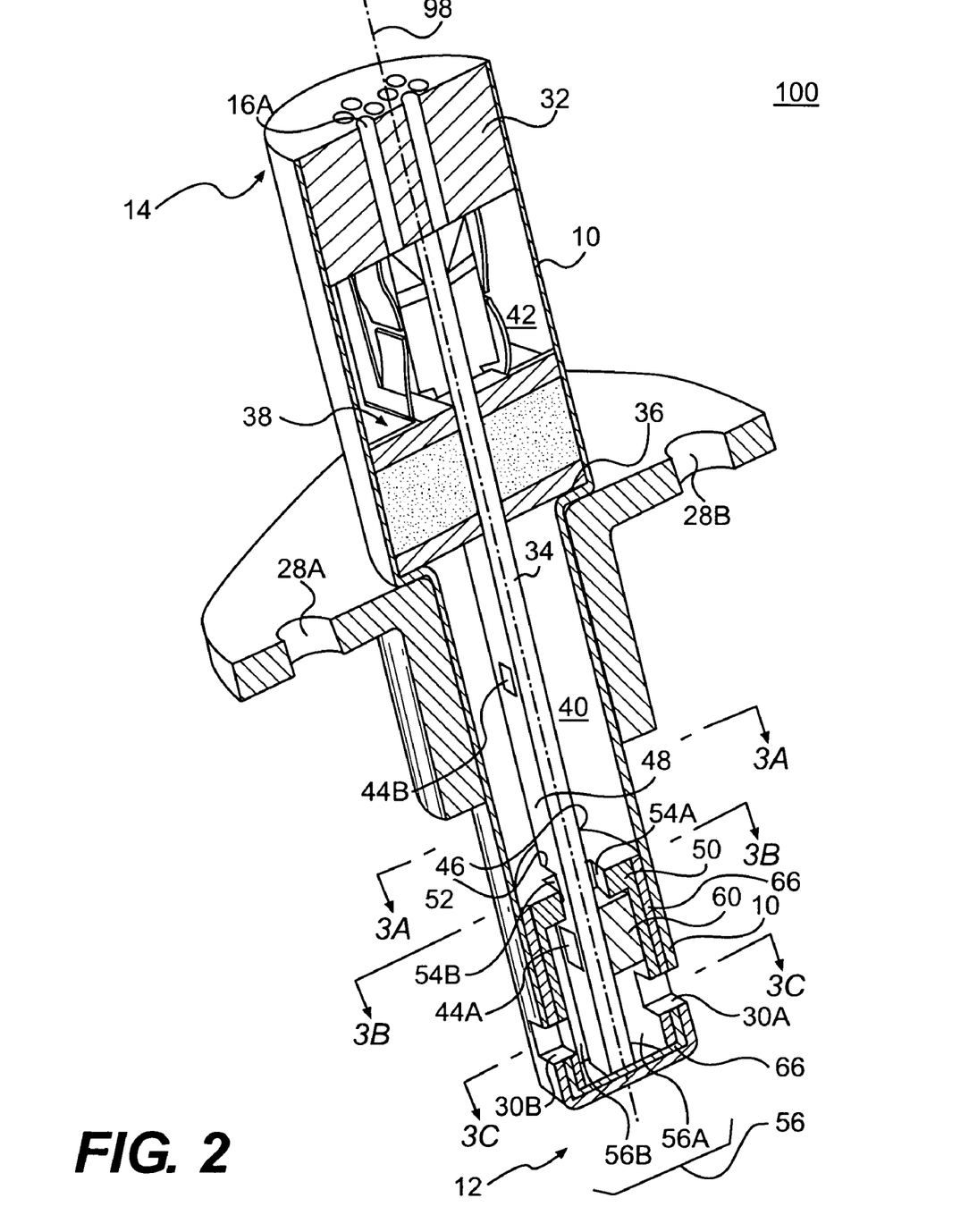
FIG. 2 is a cross-sectional illustration of the sensor of FIG. 1 along a plane 2-2 of FIG. 1.

FIG. 2 is a cross-sectional illustration of sensor assembly 100 along plane 2-2 of FIG. 1. As depicted in FIG. 2 (and FIG. 1), at second end 14 of sensor assembly 100, a grommet 32 may be inserted into housing 10 of sensor assembly 100. Wire leads 16 (not shown in FIG. 2) may extend into housing 10 through passages 16A on grommet 32. Sensor assembly 100 may be sealed at first end 12. In some embodiments (as depicted in FIGS. 1 and 2), the material of housing 10 may seal first end 12. In some other embodiments, housing 10 may include an open cavity at first end 12. During assembly of sensor assembly 100, some components may be inserted into housing 10 through this open cavity. In these embodiments, some of these inserted components may seal first end 12 of sensor assembly 100. An enclosed space within housing 10 of sensor assembly 100 may be divided into a sampling chamber 40 and a sealed chamber 42 by a sealing assembly 38 positioned within housing 10 between grommet 32 and a step 36 of housing 10. A sensing element 34 may be disposed longitudinally within housing 10, and may extend through sealing assembly 38 from first end 12 towards second end 14. Sealing assembly 38 may include parts that form a substantially exhaust tight seal between sensing element 34 and housing 10 located between sampling chamber 40 and sealed chamber 42. Any method known in the art may be used to form a tight seal around sensing element 34 using sealing assembly 38. In one embodiment, sealing assembly 38 may include a powder material, sandwiched between two plates to form a tight seal around sensing element 34.

Sensing element 34 may be of a multilayer ceramic construction, and may be configured to determine the level of one or more constituents of the exhaust stream. Sensing element 34 may include one or more sensing regions (a first sensing region 44A and a second sensing region 44B) on a second side 48 (opposite a first side 46) of sensing element 34. Although both first sensing region 44A and second sensing region 44B are shown to be on the same side of sensing element 34, in general, sensing regions can be positioned on the same or opposite sides of sensing element 34. These sensing regions may each be configured to measure a separate constituent of the exhaust gases. In some embodiments, first sensing region 44A may be configured to measure the concentration of oxygen in the exhaust gases and second sensing region 44B may be configured to measure the concentration of $NO_x$ in the exhaust gases. One or more heating elements may also be embedded in the sensing element 34. In some embodiments, separate heating elements may be embedded below each sensing region to heat each sensing region independently. Wire leads 16 (not shown in FIG. 2), that extends into housing 10 through passages 16A on grommet 32, may be coupled to sensing element 34 proximate second end 14. An opposite end of the wire leads 16, external to housing 10, may be coupled to a controller (not shown) which may be configured to operate sensor assembly 100. Operating sensor assembly 100 may include transmitting power to the heating elements and recording data from the sensing regions. Since sensing element 34, of the type described herein, is well known in the art, details of the operation of sensing element 34 is not included herein.

At first end 12, sensing element 34 may extend into a sleeve 50. Sleeve 50 may substantially enclose a region of sensing element 34 at first end 12. This enclosed region may include one or more sensing regions of sensing element 34. In some embodiments, as depicted in FIG. 2, first sensing region 44A may be located in a region enclosed by sleeve 50, and second sensing region 44B may be located in the sampling chamber 40. In some embodiments, both first sensing region 44A and second sensing region 44B may be located in sampling chamber 40, and sleeve 50 may not enclose any sensing region of sensing element 34.

Figures 3A, 3B, 3C:
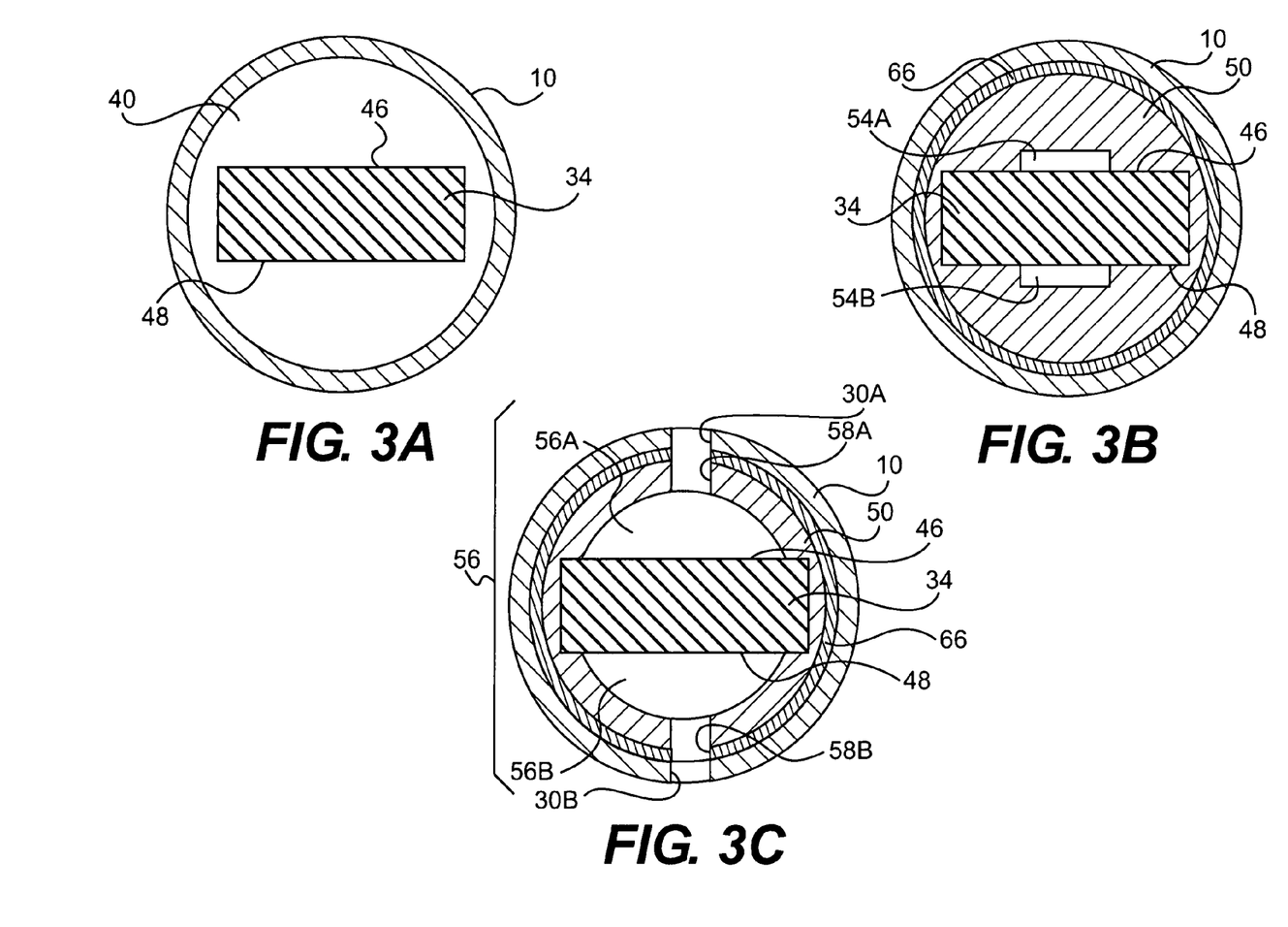
FIGS. 3A-3C are cross-sectional illustrations of the sensor of FIG. 1 along planes 3A-3A, 3B-3B, and 3C-3C of FIG. 2.

FIGS. 3A-3C illustrate three cross-sectional views of sensor assembly 100 along planes 3A, 3B, and 3C (marked in FIG. 2), normal to longitudinal axis 98. In the discussion that follows reference will be made to FIGS. 3A-3C. In the sampling chamber 40 (see FIG. 3A), housing 10 may be circumferentially disposed around, and in a spaced relationship with, sensing element 34. In this region, any gas (such as, for example, exhaust gas) within housing 10 may flow from first side 46 to second side 48 of sensing element 34 around the sensing element 34. Proximate first end 12, sensing element 34 may extend into sleeve 50 through a recess on sleeve 50 (see FIG. 3B). This recess may be sized such that when the sensing element 34 extends into sleeve 50, passages may be formed on either side. That is, a first channel 54A may be formed on first side 46 of sensing element 34, and a second channel 54B may be formed on second side 48 of sensing element 34. In a region of housing 10 enclosed by sleeve 50 (see FIG. 3C), an enclosed space 56 within sleeve 50 may be divided into a first passageway 56A on first side 46 of sensing element 34 and a second passageway 56B on second side 48 of sensing element 34. In this region, sensing element 34 may block any gas in enclosed space 56 from moving between first passageway 56A and second passageway 56B. That is, gas in enclosed space 56 may move from first passageway 56A to second passageway 56B only by exiting first passageway 56A through first channel 54A, moving from first side 46 to second side 48 of sensing element 34 in sampling chamber 40, and then entering second passageway 56B through second channel 54B. First passageway 56A may include a catalyst assembly 60 configured to direct exhaust gases therethrough. Sleeve 50 may also include an inlet orifice 58A and an outlet orifice 58B that aligns with inlet port 30A and outlet port 30B, respectively, of housing 10.

During operation, exhaust gas may be directed into first passageway 56A through the inlet port 30A and inlet orifice 58A (see, FIG. 3A). While in first passageway 56A, these exhaust gases may pass through catalyst assembly 60 and enter sampling chamber 40 through first channel 54A. The exhaust gases may flow past the sensing regions of the sensing element 34 in sampling chamber 40, and enter second passageway 56B through second channel 54B (see FIG. 3B). These exhaust gases may then exit the housing through outlet port 30B and outlet orifice 58B (see FIG. 3C).

Figure 4:
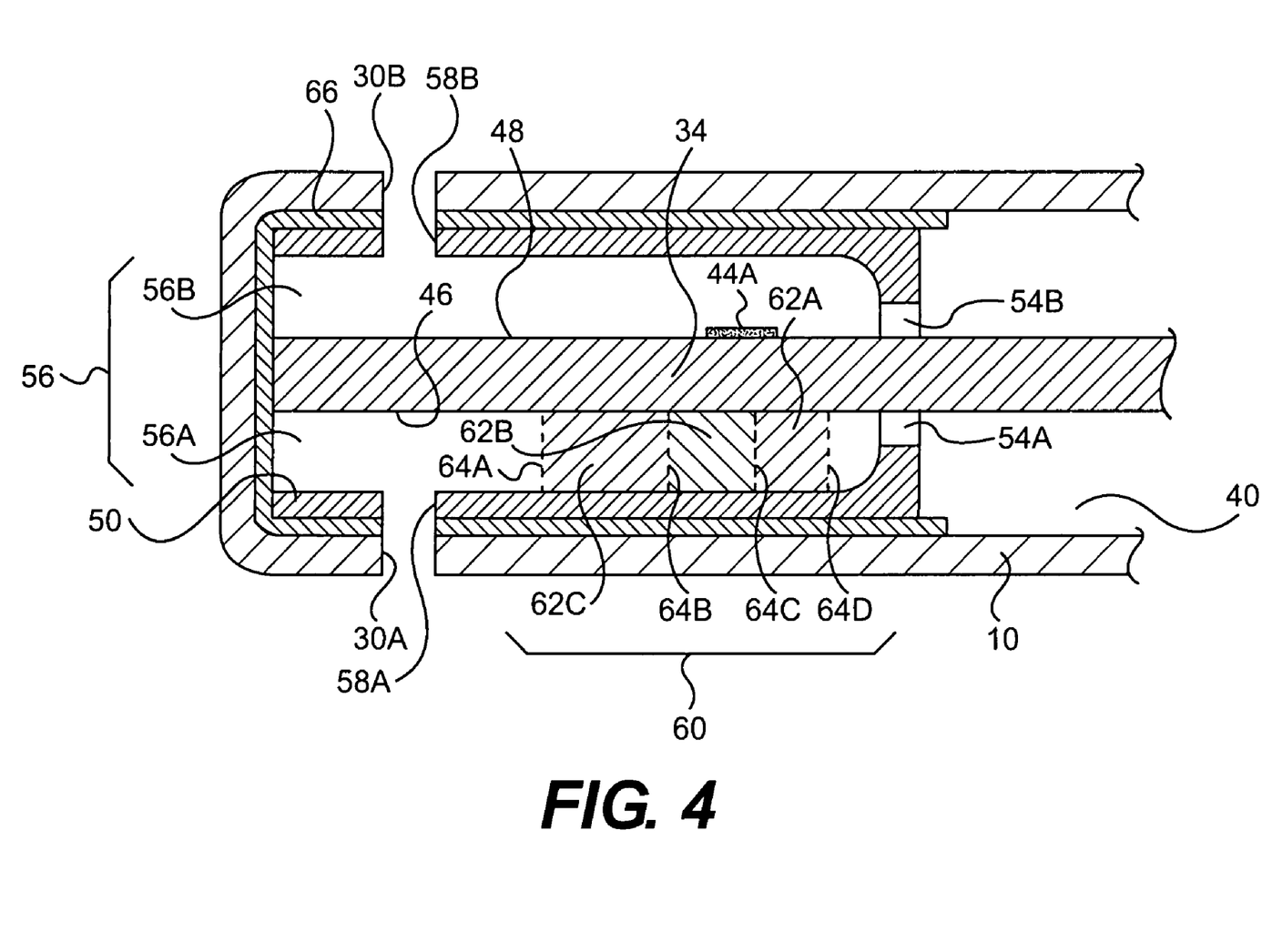
FIG. 4 is an illustration of an embodiment of a catalyst assembly of the sensor of FIG. 1.

FIG. 4 illustrates an embodiment of catalyst assembly 60 that may be included in first passageway 56A. Catalyst assembly 60 may be in physical contact with the sensing element 34. During operation, catalyst assembly 60 may get heated by the heat conducted from sensing element 34. Catalyst assembly 60 may be positioned in first passageway 56A such that exhaust gases may pass through catalyst assembly 60 before entering sampling chamber 40. Catalyst assembly 60 may include one or more catalysts to condition exhaust gases. Conditioning exhaust gases may include chemically converting an exhaust gas constituent into another constituent to increase the sensitivity of measurement. Catalyst assembly 60 may include any number of catalysts configured to condition exhaust gases. In the embodiment illustrated in FIG. 4, catalyst assembly 60 includes three catalysts (62A, 62B, 62C) separated with a mesh (64A, 64B, 64C, and 64D) placed on either side of each catalyst. Mesh (64A, 64B, 64C, and 64D) may be any part that is configured to keep catalysts (62A, 62B, 62C) separated while allowing a gas to flow through. Mesh (64A, 64B, 64C, and 64D) may include a wire mesh, a porous ceramic part, or any other part that may serve its function. The catalysts may be any type of catalyst known in the art. For example, catalyst 62A may be an oxidation catalyst (such as, platinum loaded γ-alumina pellets) to convert NO to $NO_2$; catalyst 62B may be a catalyst configured to oxidize particulate matter, such as $CH_4$, CO, etc; and catalyst 62C may include an absorber material, such as calcium oxide (CaO). It should be emphasized that the illustration of catalyst assembly 60 in FIG. 4 is exemplary only, and in general, any type of catalyst known in the art may be used as catalyst assembly 60.

Sleeve 50 may be made of any material that is a poor conductor of heat. The poor thermal conductivity of sleeve 50 may reduce the heat transfer between catalyst assembly 60 and housing 10 of sensor assembly 100. In an exemplary embodiment, sleeve 50 may be made of a ceramic material. Any known method maybe used to fabricate sleeve 50. In some embodiments, a sintering based method may be used. In these embodiments, a slurry of a ceramic powder (along with organic compounds such as plasticizers, binders, etc.) may be cast to a desired shape of sleeve 50, and sintered. In some embodiments, sleeve 50 may be fabricated as multiple parts which are then joined together. In some embodiments, an additional sealant material 66 may be provided between sleeve 50 and housing 10 to reduce the heat transfer between the sleeve 50 and the housing 10. Sealant material 66 may also minimize seepage of exhaust gas between sleeve 50 and housing 10, and thereby minimize unconditioned exhaust gases from leaking into sampling chamber 40 bypassing the catalyst. In some embodiments, sealant material 66 may comprise multiple materials or multiple pieces of the same material. For instance, one piece of sealant material 66 may be provided between the side walls of sleeve 50 and housing 10 while another piece of sealant material 66 may be provided between the base of sleeve 50 and housing 10.

Figure 5A:
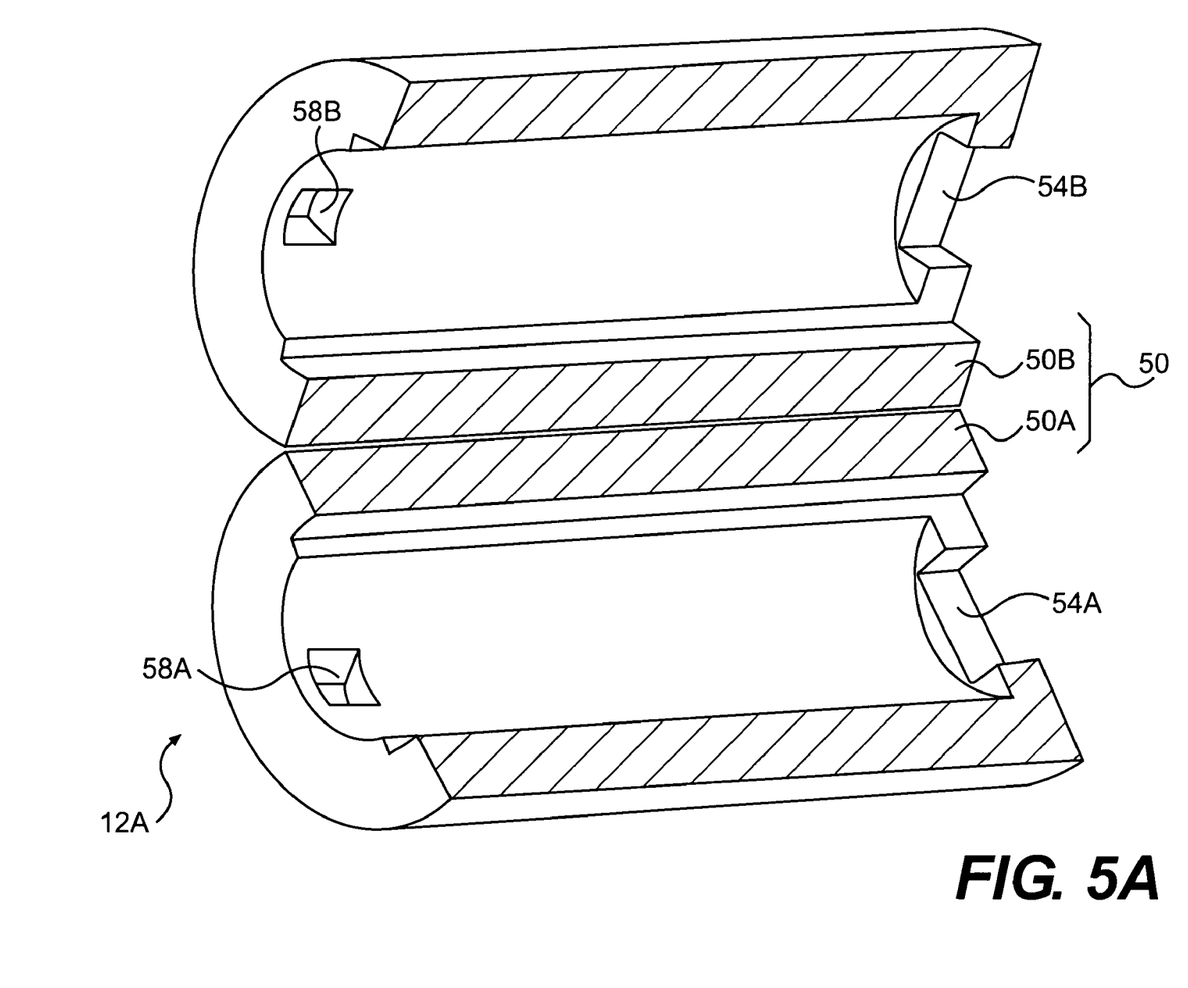
FIG. 5A-5C are schematic illustrations of an embodiment of a sleeve of the sensor of FIG. 1.
Figure 5B:
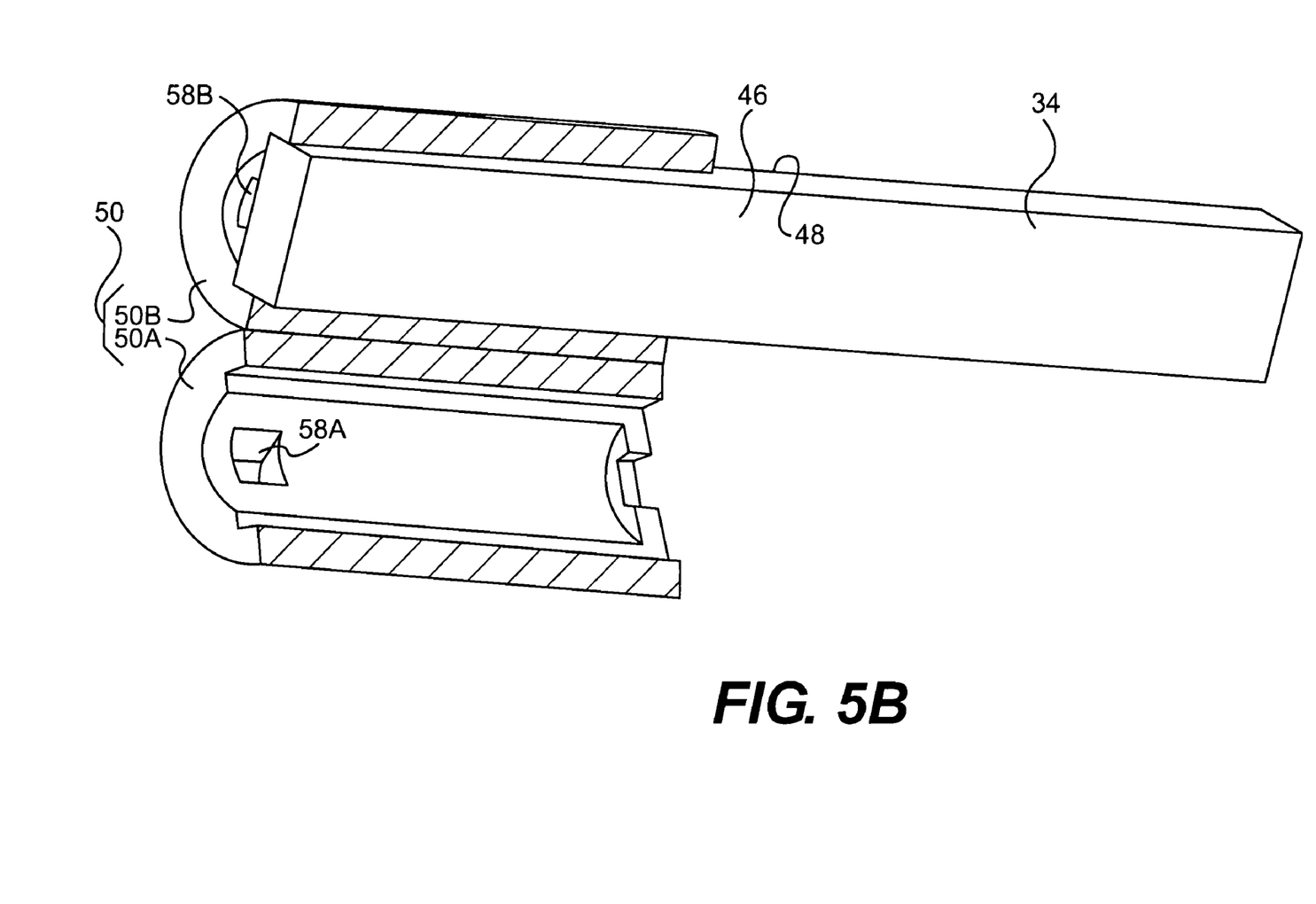
Figure 5C:
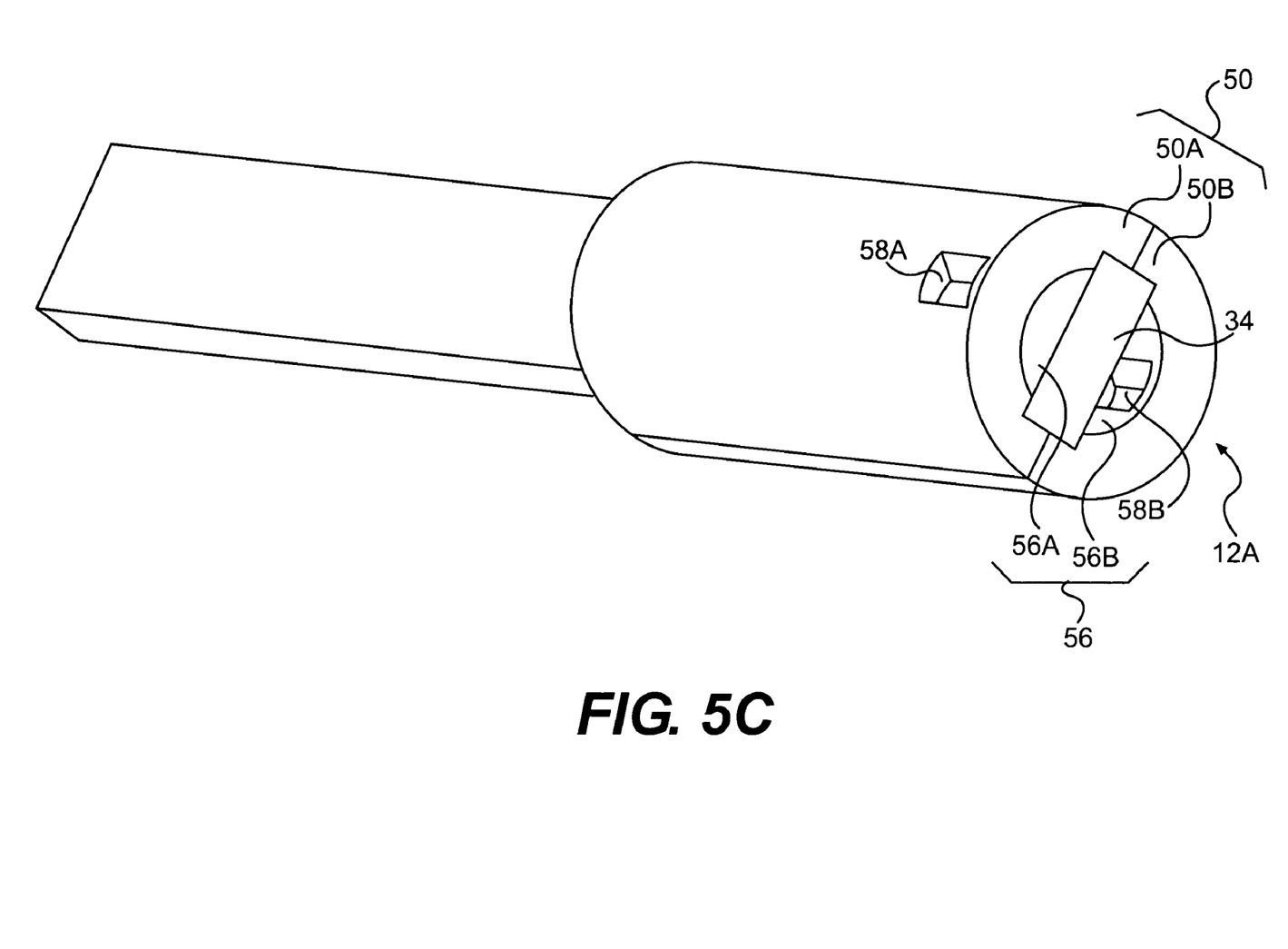

FIGS. 5A-5C illustrate sleeve 50 at different stages of fabrication. As indicated in FIG. 5A, sleeve 50 may be fabricated as two halves, a first half 50A and a second half 50B. As indicated earlier, any process known in the art may be used to fabricate first half 50A and second half 50B. The two halves of sleeve 50 may include shapes that form the features of sleeve 50 after assembly. For instance, first half 50A and second half 50B may include recesses and cavities configured to snugly hold sensing element 34 between them. First half 50A may also include a recess that forms first channel 54A, and second half 50B may include a recess that forms second channel 54B, when first half 50A and second half 50B are joined around sensing element 34 (see FIG. 5C). In some embodiments, first end 12A of sleeve may be open as illustrated in FIG. 5A. However, it is contemplated that, in other embodiments, first end 12A of sleeve 50 may be closed. Inlet orifice 58A and outlet orifice 58B may also be formed, proximate first end 12A, on first half 50A and second half 50B, respectively. Although, in general, sleeve 50 may have any shape, in some embodiments, an external shape of sleeve 50 may match an internal shape of housing 10. In some embodiments, an external surface of sleeve 50, and a mating internal surface of housing 10, may include keying features (not shown), that may allow orienting and/or positioning sleeve 50 in a desired manner within housing 10.

As illustrated in FIG. 5B, the two halves may be joined together, around the sensing element 34, by placing sensing element 34 between the first half 50A and second half 50B of sleeve 50. The mating surfaces of the two halves may then be attached to form sleeve 50 with the sensing element 34 held snugly therebetween. Any method known in the art may be used to attach the two halves of sleeve 50 together. In some embodiments, a bonding material (such as glass paste) may be applied on the mating faces between the two halves before they are brought together. The first half 50A and second half 50B, with the bonding material between the mating faces may be heated to the bonding temperature to bond the two halves together and form sleeve 50. It is also contemplated that the two halves may be joined by other methods. For instance, in some embodiments, the two halves may be cofired to form sleeve 50. In these embodiments, a first half 50A and second half 50B may be cast from a slurry of the ceramic powder and organic binders/plasticizers mixed together. In this form, the cast parts may be relatively flexible. This relatively flexible form of a ceramic part may be referred in the art as a green part. The first half 50A and second half 50B, in their green state, may be joined together with the sensing element 34 placed therebetween, and the assembly heated to the sintering temperature. Sintering may densify and join the first half 50A and second half 50B together to form sleeve 50 around sensing element 34. It is also contemplated that, in some embodiments, sensing element 34 may also be cofired with first half 50A and second half 50B to form a unitary structure of sleeve 50 and sensing element 34.

FIG. 5C illustrates sensing element 34 with sleeve 50 formed around it. Catalyst assembly 60 may now be inserted into first passageway 56A. Catalyst assembly 60 may be inserted into first passageway 56A by any means. In some embodiments, components of catalyst assembly 60 may be individually inserted into first passageway 56A to form catalyst assembly 60. In one such embodiment, a mesh 64A or other porous material of a desired size and shape (see FIG. 4) may be first inserted into first passageway 56A through first end 12. Catalyst 62C, in the form of powder, may then be poured/placed into first passageway 56A and compacted against mesh 64A. Mesh 64B may then be placed over the compacted catalyst 62C, and catalyst 62B placed over mesh 64B. The individual catalysts may thus be placed and compacted to form catalyst assembly 60. It should be emphasized that the illustrated process is exemplary only, and that catalyst assembly 60 may be inserted into first passageway 56A by any alternate methods. For instance, a prefabricated catalyst assembly 60 may be inserted into first passageway 56A. In the embodiment of sleeve 50 illustrated in FIGS. 5A-5C, catalyst assembly 60 may be in direct contact with first side 46 of sensing element 34. During operation, catalyst assembly 60 may be heated by the heat transferred from heating elements embedded within sensing element 34. The configuration of sleeve 50 illustrated in FIGS. 5A-5C is exemplary only, and sleeve 50, in general, may have any configuration.

Figure 6A:
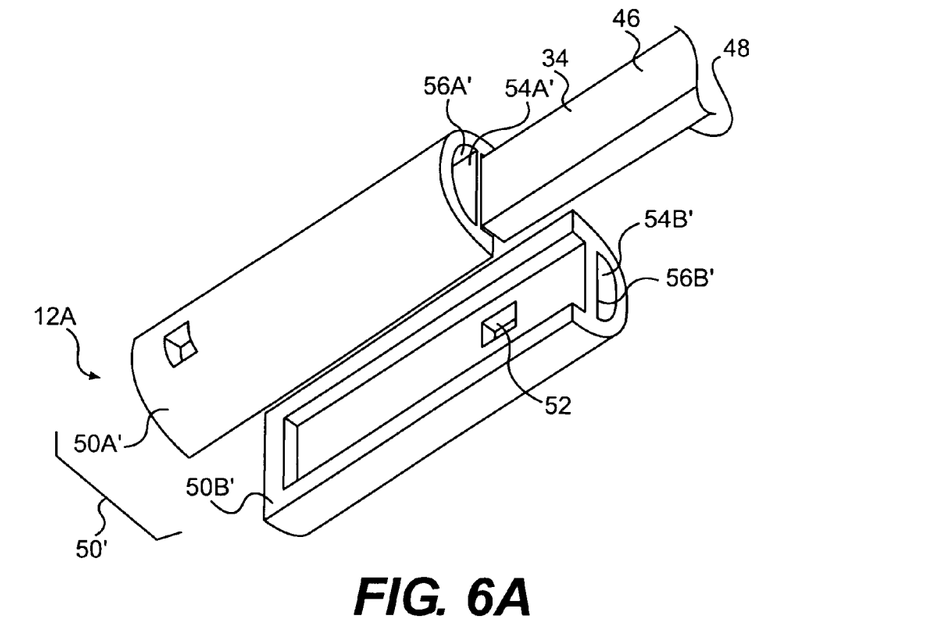
FIG. 6A-6B are schematic illustrations of another embodiment of a sleeve of the sensor of FIG. 1.
Figure 6B:
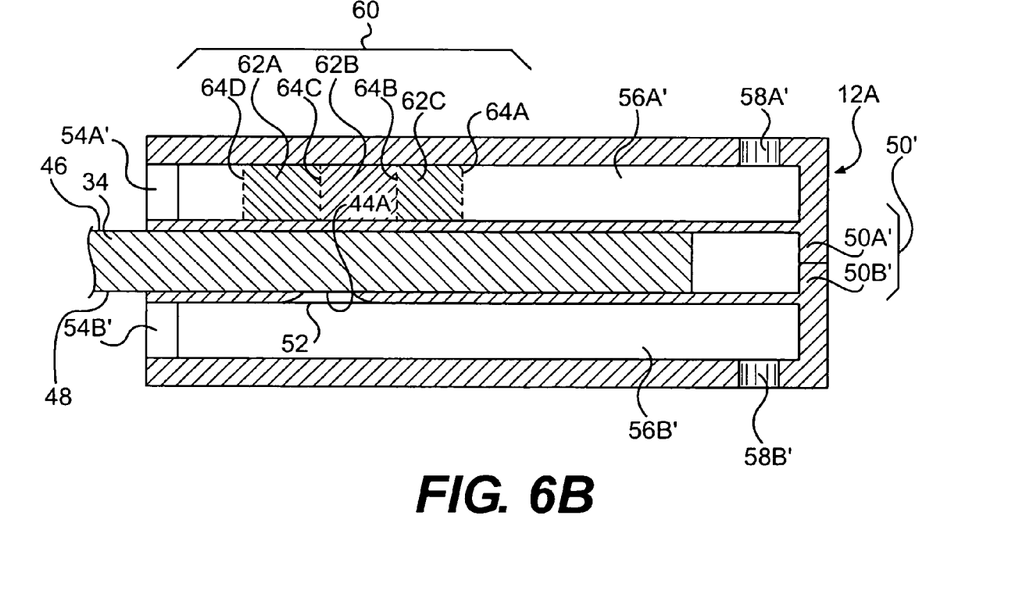

FIGS. 6A-6B illustrate another embodiment of sleeve 50' that may be used with sensor assembly 100. In the embodiment of sleeve 50' depicted in FIGS. 6A-6B, first passageway 56A' and second passageway 56B' may be closed at first end 12A. Additionally, a longitudinal recess may be formed on sleeve 50' to insert sensing element 34 therein. Sleeve 50' may also be formed as two halves, a first half 50A' and a second half 50B', that may be joined together to form sleeve 50'. In some embodiments, a wall of sleeve 50' may separate sensing element 34 from first passageway 56A' and second passageway 56B'. An opening 52 on second half 50B' of sleeve 50' may expose a region of sensing element 34 to exhaust gases in second passageway 56B'. When sensing element 34 is assembled within sleeve 50', the region of sensing element 34 exposed to second passageway 56B' may correspond to first sensing region 44A. In embodiments of sensor assembly 100 with all sensing regions in sampling chamber 40, this opening 52 may be eliminated. As in the previous embodiment, inlet orifice 58A' and outlet orifice 58B' may be formed on first half 50A' and second half 50B' of sleeve 50', respectively. First half 50A' may also include a catalyst assembly 60 to condition the exhaust gases flowing through first passageway 56A'. The wall of sleeve 50' that separates first passageway 56A' from sensing element 34 may separate catalyst assembly 60 from sensing element 34. In these embodiments, catalyst assembly 60 may get heated by the heat conducted to catalyst assembly 60 through the wall that separates the sensing element 34 and catalyst assembly 60. Since first end 12A of sleeve 50' is closed, this catalyst assembly 60 may be inserted into sleeve 50' through first channel 54A' using a similar process as described with respect to sleeve 50.

Sleeve 50 (or sleeve 50'), with sensing element 34 and catalyst assembly 60 included therein, may then be assembled into housing 10 (see FIG. 2). To assemble sleeve 50 (or 50') into housing 10, the assembled sleeve 50 (or 50') may be inserted into housing 10 through second end 14. In some embodiments, sealant material 66 may be included between sleeve 50 (or 50') and housing 10. This sealant material 66 may substantially prevent flow of exhaust gases through a space between housing 10 and sleeve 50 (or 50'). In some embodiments, the sealant material 66 may be a thermally insulating material. This insulating material may reduce thermal transfer between sleeve 50 (or 50') and housing 10. Sleeve 50 (or 50') may be oriented within housing 10 such that inlet orifice 58A and outlet orifice 58B of sleeve 50 (or 50') are aligned with inlet port 30A and outlet port 30B, respectively, of housing 10. After locating sleeve 50 (or 50') at first end 12 of housing 10, sealing assembly 38 maybe formed to couple sensing element 34 to housing 10. The sealing assembly 38 may also form an exhaust tight seal around sensing element 34.

INDUSTRIAL APPLICABILITY

The presently disclosed sensor assembly may be used in any application where it is desirable to measure the constituents of a fluid. One application of the disclosed sensor assembly may include measuring the constituents of exhaust gases from an engine. The thermally insulating sleeve of the sensor maintains the catalyst of sensor assembly in close proximity to the heaters embedded in the sensing elements, and also reduces the loss of heat from the catalyst to the exhaust gases flowing around the sensor. This reduction in heat loss may decrease the power needed by the heating elements to maintain the catalyst at a desired temperature. The operation of sensor assembly 100 will now be described. In the discussion that follows, sensor assembly 100 is assumed to be positioned in an exhaust duct that transports exhaust gases from an engine.

As the exhaust gases flow by sensor assembly 100 in exhaust duct, a portion of the exhaust gases may be driven into first passageway 56A (or 56A') of sleeve 50 (or 50') through inlet port 30A. These exhaust gases may proceed to sampling chamber 40 through catalyst assembly 60. During operation of the sensor assembly 100, heating elements embedded in the sensing element 34 may be powered to heat the sensing regions (first sensing region 44A and second sensing region 44B) to a desired temperature. The catalyst assembly 60, positioned within sleeve 50 (or 50'), in close proximity to sensing element 34, may also be heated to a desired temperature by the heat conducted from sensing element 34. As the exhaust gases flow through catalyst assembly 60, the exhaust gases may be conditioned. Heating the catalyst assembly 60 to a desired temperature may increase the efficiency of catalyst assembly 60 to condition exhaust gases. This conditioned exhaust gases may enter sampling chamber 40 through first channel 54A (or 54A') of sleeve 50 (or 50'). The exhaust gases may then travel through sampling chamber 40 and flow over the sensing regions on the second side 48 of sensing element 34. As the exhaust gases flow though sampling chamber 40 and second passageway 56B (or 56B'), the sensing regions may measure some of the constituents of the exhaust gases. These exhaust gases may then exit the housing 10 through outlet orifice 58B.

As the thermally insulating sleeve reduces heat loss from the sensor assembly 100 to exhaust gases, the sensing element 34 and the catalyst assembly 60 may be maintained at a desired temperature without increasing the power supplied to the heating elements of the sensor assembly 100. Reducing the power needed to operate sensor assembly 100 may increase the efficiency of sensor assembly.

It will be apparent to those skilled in the art that various modifications and variations can be made to the sensor assembly of the present disclosure. Other embodiments will be apparent to those skilled in the art from consideration of the specification and practice of the disclosed sensor assembly. It is intended that the specification and examples be considered as exemplary only, with a true scope being indicated by the following claims and their equivalents.

I claim:

1. A sensor assembly comprising:
a housing, the housing including an inlet port and an outlet port;
a sensing element disposed within the housing extending along a longitudinal axis from a first end towards a second end, the sensing element including heating elements; and
a sleeve circumferentially disposed about the sensing element, the sleeve including,
a first passageway on a first side of the sensing element and a second passageway on an opposite second side of the sensing element, the first passageway and the second passageway being longitudinal passageways extending along a length of the sensing element, and
an inlet orifice on one side of the sleeve and an outlet orifice on an opposite side of the sleeve, the inlet orifice fluidly coupling the inlet port with the first passageway and the outlet orifice fluidly coupling the outlet port with the second passageway.

2. The sensor assembly of claim 1, wherein the sleeve is made of a ceramic material.

3. The sensor assembly of claim 1, wherein the first passageway and the second passageway are fluidly separated within the sleeve.

4. The sensor assembly of claim 1, wherein the sleeve has a substantially cylindrical external shape and the inlet orifice and the outlet orifice are positioned on diametrically opposite sides of a curved wall of the sleeve.

5. The sensor assembly of claim 1, wherein the sensing element includes at least one sensing region, the at least one sensing region being configured to measure a concentration of a constituent of a fluid passing through the housing.

6. The sensor assembly of claim 1, wherein the first passageway and the second passageway are fluidly coupled to a sampling chamber within the housing and positioned external to the sleeve.

7. The sensor assembly of claim 6, wherein the sleeve is configured to input a fluid passing outside the housing to the sampling chamber through the inlet orifice and the first passageway, and output the fluid to the outside of the housing through the second passageway and the outlet orifice. *

8. The sensor assembly of claim 1, including a catalyst assembly disposed in the first passageway. *

9. The sensor assembly of claim 8, wherein the catalyst assembly is in physical contact with the first side of the sensing element. *

10. The sensor assembly of claim 8, wherein the catalyst assembly is physically separated from the sensing element by a wall of the sleeve.

11. A method of measuring a concentration of a constituent of exhaust gases using a sensor, comprising:
directing exhaust gases into a housing of the sensor through an inlet port of the housing;
conditioning the exhaust gases by passing the exhaust gases through a catalyst assembly, the catalyst assembly being positioned in a first passageway of a sleeve, the sleeve being positioned inside the housing and circumferentially disposed about a sensing element of the sensor, the first passageway extending longitudinally along a first side of the sensing element;
passing the conditioned exhaust gases to a sampling chamber of the sensor, the sampling chamber being a region of the sensor including at least one sensing region of the sensor;
directing the exhaust gases from the sampling chamber to a second passageway of the sleeve, the second passageway being disposed on a second side of the sensing element opposite the first side; and
directing exhaust gas from the second passageway to outside the housing through an outlet port of the housing, the outlet port being positioned opposite the inlet port.

12. The method of claim 11 further including, heating the catalyst assembly by powering heating elements included in the sensing element.

13. The method of claim 11, wherein directing exhaust gases into the housing includes directing exhaust gases from the inlet port to the first passageway through an inlet orifice of the sleeve.

14. The method of claim 11, wherein directing exhaust gas from the second passageway includes directing the exhaust gases from the second passageway to the outlet port through an outlet orifice of the sleeve.

15. A sensor assembly for measuring constituents of an exhaust gas, comprising:
an external housing extending from a first end to a second end along a longitudinal axis;
a sensing element extending from the first end towards the second end,
a substantially cylindrical sleeve located proximate the first end, the sleeve being circumferentially disposed about the sensing element and positioned radially inwards of the housing, the sleeve including,
a first passageway extending from a sampling chamber of the sensor assembly to an inlet orifice proximate the first end, along a first side of the sensing element, and
a second passageway extending from the sampling chamber to an outlet orifice proximate the first end, along a second side of the sensing element opposite the first side; and
a catalyst assembly disposed in the first passageway.

16. The sensor assembly of claim 15 wherein, the sleeve is made of a ceramic material.

17. The sensor assembly of claim 15, wherein the inlet orifice and the outlet orifice are located diametrically opposite each other, and the housing further includes an inlet port that aligns with the inlet orifice and an outlet port that aligns with the outlet orifice.

18. The sensor assembly of claim 15, further including a sealing material between an external surface of the sleeve and an internal surface of the housing.

19. The sensor assembly of claim 15, wherein the sensing element includes embedded heating elements and the second side of the sensing element includes sensing regions.

20. The sensor assembly of claim 15, wherein the catalyst assembly is in physical contact with the first side of the sensing element.

* * * * *